United States Patent
Hull et al.

(10) Patent No.: US 11,148,134 B2
(45) Date of Patent: Oct. 19, 2021

(54) ASSAY DEVICE MEASURING VISCOSITY AND DETECTING OR MEASURING A BIOMAKER

(71) Applicant: SEPSENSE LIMITED, Chester (GB)

(72) Inventors: Peter Hull, Cheshire (GB); Jimish Patel, Bodelwyddum (GB)

(73) Assignee: SEPSENSE LIMITED, Chester (GB)

( * ) Notice: Subject to any disclaimer, the term of this patent is extended or adjusted under 35 U.S.C. 154(b) by 268 days.

(21) Appl. No.: 16/080,073

(22) PCT Filed: Feb. 23, 2017

(86) PCT No.: PCT/GB2017/050474
§ 371 (c)(1),
(2) Date: Aug. 27, 2018

(87) PCT Pub. No.: WO2017/149277
PCT Pub. Date: Sep. 8, 2017

(65) Prior Publication Data
US 2019/0083973 A1 Mar. 21, 2019

(30) Foreign Application Priority Data

Mar. 3, 2016 (GB) ..................................... 1603705

(51) Int. Cl.
*B01L 3/00* (2006.01)
*G01N 33/487* (2006.01)
(Continued)

(52) U.S. Cl.
CPC ............. *B01L 3/502* (2013.01); *B01L 3/5027* (2013.01); *G01N 33/487* (2013.01); *G01N 33/53* (2013.01);
(Continued)

(58) Field of Classification Search
CPC .................. B01L 3/502; B01L 3/5027; B01L 2300/0654; B01L 2300/0816;
(Continued)

(56) References Cited

U.S. PATENT DOCUMENTS 5,792,660 A * 8/1998 Spillert .................. G01N 11/16
422/504
6,454,945 B1 * 9/2002 Weigl ................. B01D 11/0492
204/600
(Continued)

FOREIGN PATENT DOCUMENTS

EP 2581744 * 4/2013
EP 2581744 A1 4/2013
(Continued)

OTHER PUBLICATIONS

International Search Report and Written Opinion for International Application No. PCT/GB2017/050474, dated Apr. 28, 2017, 13 pages.
(Continued)

*Primary Examiner* — Matthew D Krcha
*Assistant Examiner* — Jacqueline Brazin
(74) *Attorney, Agent, or Firm* — Hoffman Warnick LLC (57) ABSTRACT

An assay device for use with samples of biological fluid, the assay device comprising: a physical detection unit for measuring a viscosity of a biological fluid sample; and a biomarker detection unit for detecting and/or measuring a biomarker in the biological fluid sample, wherein the physical detection unit and the biomarker detection unit act together as part of an assay process.

19 Claims, 6 Drawing Sheets

(51) Int. Cl.
*G01N 33/53* (2006.01)
*G01N 33/574* (2006.01)
*G01N 33/68* (2006.01)
*G01N 21/31* (2006.01)

(52) U.S. Cl.
CPC ... *G01N 33/57484* (2013.01); *G01N 33/6893* (2013.01); *B01L 2200/04* (2013.01); *B01L 2300/02* (2013.01); *B01L 2300/0627* (2013.01); *B01L 2300/0654* (2013.01); *B01L 2300/0681* (2013.01); *B01L 2300/0809* (2013.01); *B01L 2300/0816* (2013.01); *B01L 2300/0883* (2013.01); *B01L 2400/0406* (2013.01); *G01N 21/31* (2013.01)

(58) Field of Classification Search
CPC ......... B01L 2300/0883; B01L 2200/04; B01L 2300/02; B01L 2300/0627; B01L 2300/0809; B01L 2300/0681; B01L 2400/0406; G01N 33/53; G01N 33/57484; G01N 33/6893; G01N 33/487; G01N 21/31; G01N 33/49; G01N 33/4905
USPC .......................................................... 422/412
See application file for complete search history.

(56) References Cited

U.S. PATENT DOCUMENTS

| | | | | |
|---|---|---|---|---|
| 2004/0189311 A1* | 9/2004 | Glezer | .................. | G01N 21/76 324/444 |
| 2007/0275415 A1* | 11/2007 | Srinivasan | .......... | B01F 13/0071 435/7.4 |
| 2008/0297169 A1* | 12/2008 | Greenquist | ............ | G01N 33/49 324/600 |
| 2012/0135511 A1* | 5/2012 | Battrell | .............. | G01N 21/6456 435/287.2 |
| 2013/0029318 A1* | 1/2013 | Fujii | ................. | B01L 3/502753 435/5 |
| 2016/0305938 A1* | 10/2016 | Linder | .............. | B01L 3/502707 |

FOREIGN PATENT DOCUMENTS

| | | |
|---|---|---|
| JP | 2008175723 A | 7/2008 |
| WO | 0113125 A1 | 2/2001 |
| WO | 02090995 A2 | 11/2002 |
| WO | 2011071772 A2 | 6/2011 |

OTHER PUBLICATIONS

Brenner et al., "Viscoelastic and aggregometric point-of-care testing in patients with septic shock—cross-links between inflammation and haemostasis," Acta Anaesthesiologica Scandinavica, 2012, vol. 56(1), 14 pages.

Great Britain Priority Search Report for Application No. GB1603705.3, dated Nov. 22, 2016, 4 pages.

Cooke et al., "Automated Measurement of Plasma Viscosity by Capillary Viscometer," Department of Haemotology, Medical School, University of Birmingham, J Clin Pathol, May 19, 1988, pp. 1213-1216.

Lee et al., "Comparison Tests for Plasma Viscosity Measurements," International Communications in Heat and Mass Transfer, 39, Oct. 25, 2012, pp. 1474-1477.

International Preliminary Report on Patentability International Application No. PCT/GB2017/050474, dated Sep. 4, 2018, 8 pages.

* cited by examiner

ASSAY DEVICE MEASURING VISCOSITY AND DETECTING OR MEASURING A BIOMAKER

FIELD

The present invention relates to an assay device and method useful with samples of biological fluid, in particular for diagnosing and/or indicating a disease state for a patient. The disease may be any disease which causes an inflammatory response in the patient, such as a disease in which acute and chronic inflammation occurs. For example, the disease may be an infectious disease (such as sepsis), arthritis, cancer or stroke.

BACKGROUND

Various methods are known for the diagnosis and monitoring of diseases which cause an inflammatory response in the patient, such as infectious diseases, arthritis, cancer and stroke. Examples of such methods include blood and urine tests as well as imaging studies, such as X-rays, ultrasound scans and computerised tomography (CT) scans.

An example of an infectious disease is sepsis. Sepsis is triggered by an infection and results in widespread inflammation, swelling and blood clotting. The identification of sepsis can be difficult, with numerous tests being conducted in order to reach a high degree of certainty in a diagnosis. Typical tests include testing the blood clotting ability of blood and detecting and/or measuring various biomarkers in the blood. The difficulty of the testing and the need for numerous tests often results in delays in diagnosis, which can enable the disease to progress before an appropriate treatment is selected and administered to the patient, which causes distress to patients. There is, therefore, a need for a simple, efficient test which can be used to diagnose and monitor a disease which causes an inflammatory response (such as sepsis) in the patient. It would be particularly advantageous to provide a test which can be used to provide results in a timely manner in the clinical setting, i.e. within a few minutes of a biological sample being provided by the patient.

SUMMARY

It is one aim of the present invention, amongst others, to provide an assay device which can be used to diagnose a disease and/or to indicate a disease state for a disease which causes an inflammatory response (such as an infectious disease, arthritis, cancer or stroke) in a patient. Another aim of the invention is to provide such a device which is simple and efficient to use, and which can provide a substantially immediate result in a clinical setting.

The present invention provides an assay device and a method of generating an output which is a diagnosis of a disease and/or which is indicative of a disease state for a patient as set forth in the appended claims. Other features of the invention will be apparent from the dependent claims, and the description, which follows.

A first aspect of the present invention provides an assay device for use with samples of biological fluid, the assay device comprising:
  a physical detection unit for measuring a viscosity of a biological fluid sample; and
  a biomarker detection unit for detecting and/or measuring a biomarker in the biological fluid sample, wherein the physical detection unit and the biomarker detection unit act together as part of an assay process.

A second aspect of the invention provides a method of generating an output, which is a diagnosis of a disease and/or which is indicative of a disease state for a patient, the method comprising:
  receiving a biological fluid sample from a patient at an assay device, wherein the assay device comprises a physical detection unit and a biomarker detection unit;
  together measuring a viscosity of the biological fluid sample and detecting and/or measuring a biomarker in the biological fluid sample to provide viscosity and biomarker measurements; and
  operating on the viscosity and biomarker measurements together to determine the output for the patient.

A third aspect of the invention provides a method of identifying a patient having a disease that is responsive to a particular treatment for said disease, the method comprising: determining a disease state for the patient; providing a treatment appropriate to the disease; monitoring the disease state according to the method of the second aspect of the invention, and/or using the assay device according to the first aspect of the invention; and identifying the patient as responsive to the particular treatment according to changes in the monitored disease state.

A fourth aspect of the invention provides a method of assaying the efficacy of a particular treatment for a disease in a patient, said method comprising: identifying a patient having a disease; determining a disease state for the patient; providing a treatment appropriate to the disease; monitoring the disease state according to the method of the second aspect of the invention, and/or using the assay device of the first aspect of the invention; and identifying the particular treatment as effective according to changes in the monitored disease state.

The assay device and methods of the invention may be used to diagnose a disease and/or to indicate a disease state for a patient. For example, the assay device and methods of the invention may be used for diagnosis and post-diagnosis to assess the progress of any particular treatment being provided to the patient. The assay device and methods of the invention typically provide results in a few minutes, which is critical in the treatment and care of many diseases, including infectious diseases (such as sepsis), stroke and other diagnostic applications including arthritis and cancer. The assay device and methods of the invention are able to provide such timely results because they are able to act upon a biological fluid directly obtained from a patient (i.e. without the need for any prior processing of the biological fluid sample) and/or because they conduct both a physical assay and a biological assay on the biological fluid at the same time, which provides an accurate result without the need for further tests.

Throughout this specification, the term "comprising" or "comprises" means including the component(s) specified but not to the exclusion of the presence of other components.

The optional features set out herein may be used either individually or in combination with each other where appropriate and particularly in the combinations as set out in the accompanying claims. The optional features for each exemplary embodiment of the invention, as set out herein are also applicable to any other aspects or exemplary embodiments of the invention, where appropriate. In other words, the skilled person reading this specification should consider the optional features for each aspect or embodiment of the invention as interchangeable and combinable between different aspects of the invention.

The first aspect of the invention provides an assay device. The term "assay device" is used herein in relation to all aspects of the invention to mean a device that conducts an assay, i.e. which conducts an investigative, analytical procedure so as to qualitatively assess and/or measure one or more properties of a biological fluid sample.

The assay device of the first aspect of the invention is for use with a sample of biological fluid. The term "biological fluid" is used herein in relation to all aspects of the invention to mean a fluid obtained from a human or animal, particularly from a living human or animal, and includes the fluid directly obtained from the human or animal and the fluid after modification or treatment. Modification or treatment may be by any suitable method, such as by filtering and/or by dilution with or dissolving in an appropriate solvent, for example with or in a suitable buffer solution. Modification or treatment may be by molecular amplification. Examples of biological fluids include whole blood, plasma, serum, saliva, expectorate and nasal sample.

Typically, a sample of less than 500 µl is required for use in the assay device and methods of the invention. For example, a sample of from 200 to 500 µl may be used. The assay device is, for example, suitable for use with a blood sample obtained by means of a finger or heel prick procedure. The reference to the sample volume is intended to refer to the volume of the sample which is input into the assay device. The skilled person would appreciate that this volume may decrease if the sample undergoes a pre-treatment step, such as filtering. The ability to conduct the test using small volumes of biological samples makes the test easy to conduct and more comfortable for the patient.

The assay device of the first aspect of the invention comprises a physical detection unit for measuring a viscosity of a biological fluid sample. Thus, the physical detection unit measures a physical property of the biological fluid sample, namely viscosity, so as to provide a viscosity value. The skilled person would appreciate that the term "viscosity" includes dynamic viscosity and kinematic viscosity. Typically, the physical detection unit of the assay device of the invention measures the dynamic viscosity of the biological fluid sample.

The assay device of the first aspect of the invention may comprise more than one physical detection unit, but typically comprises one physical detection unit.

Suitably, the physical detection unit comprises a channel and a plurality of detectors spaced along the channel to detect movement of the biological fluid sample along the channel. Suitably, the physical detection unit measures the rate of movement of the biological fluid sample along the channel. Any suitable channel and detectors may be used, as would be appreciated by the skilled person. Suitably, the channel is a capillary channel. Suitably, the detectors are optical detectors. Examples of suitable optical detectors include complementary metal oxide semiconductor (CMOS), charge coupled device (CCD), photodiode and phototransistor detectors. One or more type of suitable optical detector may be used. In use, the detectors measure the flow rate of the biological fluid sample along the channel. The flow rate is indicative of the dynamic viscosity of the fluid.

When the channel is a capillary channel, the biological fluid sample flows through the assay device, particularly the physical detection unit and the biomarker detection unit, under capillary action without the need for an external pump. This makes the assay device compact and simple to operate, and also ensures that there is no contact between the physical and biomarker detection units (which may be housed in a removable and/or disposable detection cartridge) and other components of the device such as a processing unit, output unit and/or memory unit (when present).

The presence of the biological fluid sample in the channel, such as at the entrance of the channel, may cause the measurement of the viscosity of the sample and/or the detection and/or measurement of the biomarker to begin.

The assay device of the first aspect of the invention comprises a biomarker detection unit for detecting and/or measuring a biomarker in a biological fluid sample. Thus, the biomarker detection unit detects the presence and/or measures the amount of a biomarker or substance in the biological fluid sample, so as to provide a biomarker value. The biomarker or substance to be detected and/or measured will depend on the means for which the assay device is being used, i.e. the disease which is being diagnosed and/or the disease state that is being indicated.

The assay device of the first aspect of the invention may comprise more than one biomarker detection unit, and typically comprises one or two biomarker detection units. Typically, the biomarker detection unit(s) conduct assays which make photometric, colorimetric, turbidometric and/or conductivity measurements.

Suitably, the biomarker detection unit is for detecting and/or measuring at least one biomarker selected from Procalcitonin, C-reactive protein (CRP), cytokines, alpha-fetoprotein, beta-2-microglobulin, calcitonin, immunoglobulins, D-dimer and troponin in the biological fluid sample. The biomarker detection and/or measurement may be achieved by conducting optical absorbance measurements at a specified wavelength or at a range of wavelengths, or by conducting conductance measurements.

When the disease is an infectious disease, such as sepsis, hospital acquired infections or sexually transmitted infections (STI), the biomarker detection unit may be for measuring the amount of at least one biomarker selected from Procalcitonin, C-reactive protein (CRP) and cytokines in the biological fluid sample.

When the disease is an infectious disease, such as sepsis, the biomarker detection unit may be for conducting infectious disease testing on the biological fluid sample. By "infectious disease testing" herein we mean a test which is used to diagnose a particular infectious disease. An example of such a test is the TORCH test. The TORCH test would be well known to persons skilled in the art and includes testing for toxoplasmosis, rubella, cytomegalovirus and herpes simplex virus, typically in pregnant women.

When the disease is arthritis, such as rheumatoid arthritis or polymyalgia rheumatica, the biomarker detection unit may be for measuring the amount of C-reactive protein (CRP) in the biological fluid sample.

When the disease is cancer, such as myeloma, non-Hodgkin lymphoma, chronic lymphocytic leukemia, thyroid cancer or haematological cancer the biomarker detection unit may be for detecting and/or measuring the amount of alpha-fetoprotein (AFP), beta-2-miroglobulin (particularly for multiple myeloma and chronic lymphocytic leukemia), calcitonin (particularly for thyroid cancer) and immunoglobulins in the biological fluid sample.

When the disease is stroke, the biomarker detection unit may be for measuring the amount of D-dimer and troponin in the biological fluid sample.

When the disease is sepsis, this is often found with comorbidities (for example, arthritis, atrial fibrillation, diabetes) and the dual approach of the assay device and methods of the invention increases specificity by reducing the chance of a false positive.

The physical detection unit and the biomarker detection unit act together as part of an assay process. In other words, in the assay device of the first aspect of the invention, the same biological fluid sample is analysed in both the physical detection unit and the biomarker detection unit at substantially the same time. Typically, one portion of the biological fluid sample enters the physical detection unit and another portion of the biological fluid sample enters the biomarker detection unit. This means that both of the units provide results which are used in the diagnosis of a disease and/or the indication of a disease state for a patient. This offers the advantages of a quick and efficient test, particularly which can be used to diagnose and/or monitor a patient whilst the patient remains in the clinical setting. This enables a physician to act very quickly to treat a patient if the test results indicate a problem. Analysing the same biological fluid sample in both the physical detection unit and the biomarker detection unit at substantially the same time also offers the advantage of reducing the chance of interference. For example, an interfering substance may affect the biomarkers or the viscosity of the sample but is unlikely to affect both. Thus, the assay device of the invention may improve the accuracy of the output for a patient.

Suitably, the biomarker detection unit comprises at least one vessel in which a biological assay is conducted.

Suitably, the biomarker detection unit comprises a channel, such as a capillary channel, which may transport the biological fluid sample to the at least one vessel in which a biological assay is conducted. When the channel is a capillary channel, the biological fluid sample flows to the biomarker detection unit under capillary action without the need for an external pump.

Suitably, the physical detection unit and the biomarker detection unit are housed in a removable and/or disposable detection cartridge. Suitably, the detection cartridge is a single use cartridge, i.e. which is disposed of after a single use. Suitably, the detection cartridge comprises a lab on a chip unit.

The assay device of the first aspect of the invention may further comprise a heating element, for example to maintain the device, particularly the detection cartridge, at a substantially constant temperature of 37° C.

The assay device of the first aspect of the invention may further comprise a removable and/or disposable sample cartridge. Suitably, the sample cartridge is a single use cartridge, i.e. which is disposed of after a single use. In use, the sample cartridge is typically connected to the detection cartridge at a location where the fluid enters in order to pass through the device and undergo the assay process.

The assay device of the first aspect of the invention may further comprise a filter located at or near to a fluid introducing portion. In other words, the assay device may comprise an integrated filter. Typically, the filter may be located adjacent to the sample cartridge. The filter, when present, acts to filter the biological fluid sample in a pre-treatment step. After passing through the filter in the pre-treatment step, the biological fluid sample passes through the physical detection unit and the biomarker detection unit.

As the skilled person would appreciate, any suitable filter may be used. Examples of suitable filters include plasma filters such as a Fusion 5 filter from G E Healthcare, a Vivid filter from Pall Corporation and a Cobetter separation membrane. For example, when the biological fluid is whole blood the filter separates plasma from the whole blood, such that the plasma then enters the physical detection and biomarker detection units for analysis. The use of a filter in the assay device means that it is unnecessary to process the biological fluid sample prior to its testing in the assay device. This reduces the time required to provide an output and enables diagnosis and/or disease monitoring in the patient setting. Thus, the assay device of the invention can be used in a single step method as described herein. The use of an integrated filter in the assay device also enables the device to function with small sample volumes, for example volumes obtained by a finger or heel prick method. Volumes such as these could be significantly reduced if the sample needed prior processing in a device or method external to the assay device.

The assay device of the first aspect of the invention may further comprise a molecular amplification unit located at or near to a fluid introducing portion. In other words, the assay device may comprise an integrated molecular amplification unit. Typically, the molecular amplification unit may be located adjacent to the sample cartridge. The molecular amplification unit, when present, acts to amplify the DNA present in a biological fluid sample by a polymerase chain reaction (PCR). The molecular amplification unit comprises a DNA primer which reacts with the biological fluid sample so as to amplify the DNA therein if the sample comprises a component indicative of a particular disease.

As the skilled person would appreciate, DNA primers are designed specifically for each particular test. Typically, DNA primers are short, chemically synthesized oligonucleotides with a length of about twenty bases. They are hybridized to a target DNA, which is then copied by the polymerase.

After passing through the molecular amplification unit in the pre-treatment step, the biological fluid sample passes through the physical detection unit and the biomarker detection unit. If DNA is amplified (due to the presence of a particular disease) then the viscosity of the sample will be increased. This increase in viscosity will be detected by the physical detection unit.

The use of a molecular amplification unit is advantageous in the diagnosis and monitoring of diseases which known assays are not sensitive enough to identify. For example, the use of a molecular amplification unit is advantageous in the diagnosis and monitoring of diseases such as hospital transmitted infections and sexually transmitted infections, which are difficult to diagnose early and problematic to treat. Typically, when the assay device of the first aspect of the invention comprises a molecular amplification unit the biological fluid sample being tested is a nasal fluid or saliva diluted and/or dissolved in a suitable buffer solution. Examples of suitable buffer solutions for molecular amplification include SDS/NaCl extraction buffer and phenol-chloroform extraction buffer.

Suitably, the assay device comprises a plurality of channels for separating the biological fluid sample into suitable amounts for passing through the physical detection and biomarker detection units.

Suitably, the assay device comprises a receiving vessel or reservoir located at or near to a fluid introducing portion, preferably located adjacent to a filter or molecular amplification unit when present. In use, the receiving vessel or reservoir receives a sample of biological fluid of sufficient volume to flow into each of the physical and biomarker detection units. Preferably, the receiving vessel or reservoir is located such that, in use, the sample of biological fluid flows through the filter and/or molecular amplification unit into the receiving vessel or reservoir such that the biological fluid collects in the receiving vessel or reservoir in a volume sufficient to flow into each of the physical and biomarker detection units.

Suitably, the assay device comprises a reference unit or channel which acts as a baseline. The reference unit or channel houses a portion of the biological fluid sample prior to its entry into the biomarker detection unit for comparison with the sample after the biomarker assay has been conducted. For example, when the biomarker detection unit conducts an assay which makes colorimetric measurements, the reference unit or channel provides a baseline colour with which to compare after the assay has been conducted.

The assay device of the first aspect of the invention typically is handheld and/or portable.

The assay device of the first aspect of the invention may further comprise:
- a processing unit arranged to operate on the viscosity and biomarker measurements to determine an output; and
- an output unit arranged to provide the output to the user.

The output may comprise a diagnosis of a disease and/or any information derived from the viscosity and biomarker measurements which is indicative of a disease state for the patient. For example, when the output is information which is indicative of a disease state for a patient, the output may comprise a value for the viscosity of the biological fluid sample and a value which indicates the presence and/or amount of the particular biomarker(s) in the biological fluid sample.

The output may include information on normal ranges of viscosity and/or biomarker values for healthy patients, for comparison with the values provided for the patient being assessed.

The processing unit suitably calculates the output based on the viscosity and biomarker measurements. Any suitable calculation may be used. For example, the processing unit may calculate the dynamic viscosity of the biological fluid sample from the rate of movement of the sample.

The processing unit may calculate the dynamic viscosity of the biological fluid sample from the rate of movement of the sample using the Washburn equation:

$$L^2 = \frac{\gamma D t}{4\eta}$$

where t is the time for a liquid of dynamic viscosity $\eta$ and surface tension $\gamma$ to penetrate a distance $L$ into the capillary whose pore diameter is $D$.

The processing unit may calculate a biological value for the biological fluid sample from the detected and/or measured biomarker.

Suitably, the processing unit may use an algorithm to calculate the output, for example which uses thresholds for the viscosity and biomarker values. The algorithm may compare the viscosity and/or biomarker values to normal ranges for healthy patients, for example so as to provide a diagnosis of a disease and/or an indication of a disease state of a patient. For example, the algorithm may take the form of a decision tree or flow diagram, which contains a number of branching options where each option is chosen based on the viscosity or biomarker values.

The blood plasma of a healthy adult patient has a viscosity of from 1.12 to 1.27 mPa·s. at 37° C. This information may be provided as an output for comparison with the values provided for the patient being assessed.

The processing unit may use an algorithm which compares the measured value (at 37° C.) for the viscosity of a blood plasma sample for an adult patient with the value of from about 1.1 to about 1.3 mPa·s. at 37° C. for a healthy adult. The algorithm may determine that when the measured value is lower than about 1.1 mPa·s. or higher than about 1.3 mPa·s. then the patient may have a disease.

The blood plasma of a healthy adult has a Procalcitonin concentration of less than about 0.5 ng/ml. This information may be provided as an output for comparison with the values provided for the patient being assessed.

The processing unit may use an algorithm which compares the measured value for the concentration of Procalcitonin in a blood plasma sample for an adult patient with the value of less than about 0.5 ng/ml for a healthy adult. The algorithm may determine that when the measured value is higher than about 0.5 ng/ml, then the patient may have an infectious disease but sepsis is unlikely. The algorithm may determine that when the measured value of Procalcitonin concentration is higher than about 0.5 ng/ml and lower than about 2 ng/ml then the patient may have a systemic infection and sepsis is possible, that when the measured value of Procalcitonin concentration is higher than about 2 ng/ml and lower than about 10 ng/ml then the patient is likely to have a systemic infection and sepsis is likely, and that when the measured value of Procalcitonin concentration is higher than about 10 ng/ml then the patient has a major systemic inflammatory response indicative of sepsis.

The output unit suitably comprises a display to display the output to the operator.

The assay device of the first aspect of the invention may further comprise a memory unit to store the viscosity and biomarker measurements. The memory unit may further store outputs for one or more patients.

The assay device of the first aspect of the invention may further comprise a user input unit, for example for inputting patient details.

Suitably, the processing unit is arranged to operate to determine an output which is a diagnosis of a disease and/or which is indicative of a disease state for a patient, wherein the disease is selected from one or more of an infectious disease, arthritis, cancer and stroke, for example selected from one or more of sepsis, arthritis, hospital acquired infections, sexually transmitted infections (STI), rheumatoid arthritis, polymyalgia rheumatica, myeloma, non-Hodgkin lymphoma, chronic lymphocytic leukemia, thyroid cancer, haematological cancer and stroke.

Preferably, the processing unit is arranged to operate to determine an output which is a diagnosis of a disease and/or which is indicative of a disease state for a patient, wherein the disease is sepsis.

The second aspect of the invention provides a method of generating an output, which is a diagnosis of a disease and/or which is indicative of a disease state for a patient, the method comprising:
- receiving a biological fluid sample from a patient at an assay device, wherein the assay device comprises a physical detection unit and a biomarker detection unit;
- together measuring a viscosity of the biological fluid sample and detecting and/or measuring a biomarker in the biological fluid sample to provide viscosity and biomarker measurements; and
- operating on the viscosity and biomarker measurements together to determine the output for the patient.

Suitably, the method of the second aspect of the invention further comprises storing the viscosity and biomarker measurements in a memory unit. The method of the second aspect of the invention may further comprise storing the output(s) for one or more patients.

The method of the second aspect of the invention may be conducted using any suitable assay device, including but not limited to an assay device according to the first aspect of the invention.

In the method of the second aspect of the invention, the biomarker is selected from the amount and/or presence of at least one biomarker selected from Procalcitonin, C-reactive protein (CRP), cytokines, alpha-fetoprotein, beta-2-microglobulin, calcitonin, immunoglobulins, D-dimer and troponin in the biological fluid sample.

In the method of the second aspect of the invention, the biomarker suitably comprises an infectious disease test, such as the TORCH test as discussed above.

In the method of the second aspect of the invention, the disease is selected from one or more of an infectious disease, arthritis, cancer and stroke, for example selected from one or more of sepsis, hospital acquired infections, sexually transmitted infections (STI), rheumatoid arthritis, polymyalgia rheumatica, myeloma, non-Hodgkin lymphoma, chronic lymphocytic leukemia, thyroid cancer, haematological cancer and stroke.

In the method of the second aspect of the invention, the disease may preferably be sepsis.

The third aspect of the invention provides a method of identifying a patient having a disease that is responsive to a particular treatment for said disease, the method comprising: determining a disease state for the patient; providing a treatment appropriate to the disease; monitoring the disease state according to the method of the second aspect of the invention, and/or using the assay device according to the first aspect of the invention; and identifying the patient as responsive to the particular treatment according to changes in the monitored disease state.

The fourth aspect of the invention provides a method of assaying the efficacy of a particular treatment for a disease in a patient, said method comprising: identifying a patient having a disease; determining a disease state for the patient; providing a treatment appropriate to the disease; monitoring the disease state according to the method of the second aspect of the invention, and/or using the assay device according to the first aspect of the invention; and identifying the particular treatment as effective according to changes in the monitored disease state.

In the methods of the third and fourth aspects of the invention, the disease is suitably selected from one or more of an infectious disease, arthritis, cancer and stroke, for example selected from one or more of sepsis, hospital acquired infections, sexually transmitted infections (STI), rheumatoid arthritis, polymyalgia rheumatic, myeloma, non-Hodgkin lymphoma, chronic lymphocytic leukemia, thyroid cancer or haematological cancer and stroke.

In the methods of the third and fourth aspects of the invention, the disease may preferably be sepsis.

In the methods of the invention, together measuring a viscosity of the biological fluid sample and detecting and/or measuring a biomarker in the biological fluid sample to provide viscosity and biomarker measurements allows the monitoring of a differential response during treatment due to the complex pharmacodynamics involved. For example, some biomarkers may respond very rapidly to a particular treatment but the viscosity is known to respond more slowly so that a physician may stop treatment too early if only biomarkers are detected and/or measured. If only the viscosity is measured then a physician may believe the patient is not responding to treatment and provide the incorrect treatment or treat the patient for too long. Additionally, the differential response may allow a physician to track the progression of a disease because different biomarkers have different time profiles.

BRIEF DESCRIPTION OF DRAWINGS

For a better understanding of the invention, and to show how exemplary embodiments of the same may be carried into effect, reference will be made, by way of example only, to the accompanying diagrammatic Figures, in which.

DESCRIPTION OF EMBODIMENTS

Figure 1:
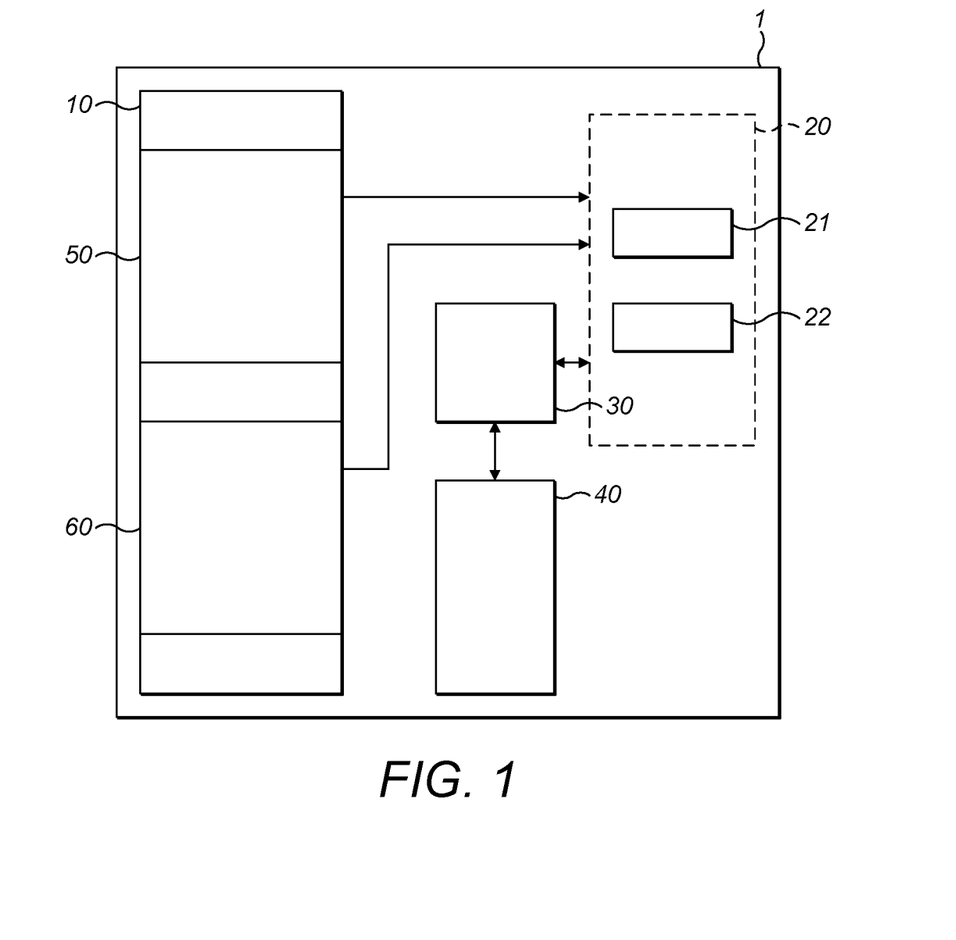
FIG. 1 shows a schematic view of an assay device according to the first aspect of the invention.

FIG. 1 shows a schematic view of an assay device 1 for use with samples of biological fluid, according to a first example embodiment of the invention. The assay device 1 of FIG. 1 comprises a detection cartridge 10, a memory unit 20, a processing unit 30 and an output unit 40. The detection cartridge 10 comprises a physical detection unit 50 and a biomarker detection unit 60.

The physical detection unit 50 and the biomarker detection unit 60 are arranged to receive the same biological fluid sample from a patient, which in this example embodiment is blood plasma. The physical detection unit 50 is arranged to measure a viscosity of the biological fluid sample. The biomarker detection unit 60 is arranged to detect and/or measure a biomarker in the biological fluid sample. In this example embodiment the biomarker detection unit 60 is arranged to detect and measure Procalcitonin levels in the biological fluid sample. However, additional and/or alternative biomarkers may be detected and/or measured in the biological fluid sample.

The memory unit 20 is arranged to store viscosity and biomarker measurements. The memory unit 20 comprises a number of storage areas. In a first storage area 21 a database including current, and optionally historical, viscosity and biomarker measurements is stored. The database further includes timestamps indicating the time at which viscosity and biomarker measurements were generated and received. The first storage area 21 may also store viscosity and biomarker values calculated by the processing unit as discussed below. In a second storage area 22 the memory unit 20 stores data used to control and inform operation of the processing unit 30, as described below.

The processing unit 30 is arranged to operate on the measurements stored in the memory unit 20 to generate an output. For example, the processing unit 30 calculates a value for the dynamic viscosity of the biological fluid sample from the rate of movement of the sample. The processing unit 30 also calculates a value for the Procalcitonin level for the biological fluid sample from the measured biomarker. Biomarkers for Procalcitonin are well known to persons skilled in the art. The processing unit 30 may also operate on the viscosity and biomarker values in the memory unit 20 to determine a diagnosis and/or an indication of a disease state for the patient.

The processing unit 30 loads the viscosity and biomarker measurements from the first memory area 21 of the memory unit 20 and operates thereon according to control data loaded from the second memory area 22 of the memory 30. As a result of the operations of the processing unit 30 values of viscosity and/or biomarker values, and/or a diagnosis and/or an indication of a disease state, are determined and passed to the output unit 40. Any of the viscosity values, biomarker values, determined diagnosis and/or indication of a disease state may be stored in the memory unit 20, particularly in the first memory area 21, to be available for later use, for example to be used at a future time so as to monitor the disease state of a particular patient.

The output unit 40 comprises a communication capability for transferring data from the device to a user. For example, the output unit 40 provides a local user with immediate feedback via a display, according to any of the determined viscosity values, biomarker values, diagnosis and/or disease state. The data may be transmitted to a remote user for review and/or storage if required.

Whilst FIG. 1 shows the detection unit adjacent to the processing, memory and output units, these units may of course be arranged in any suitable alternative arrangement.

Figure 2:
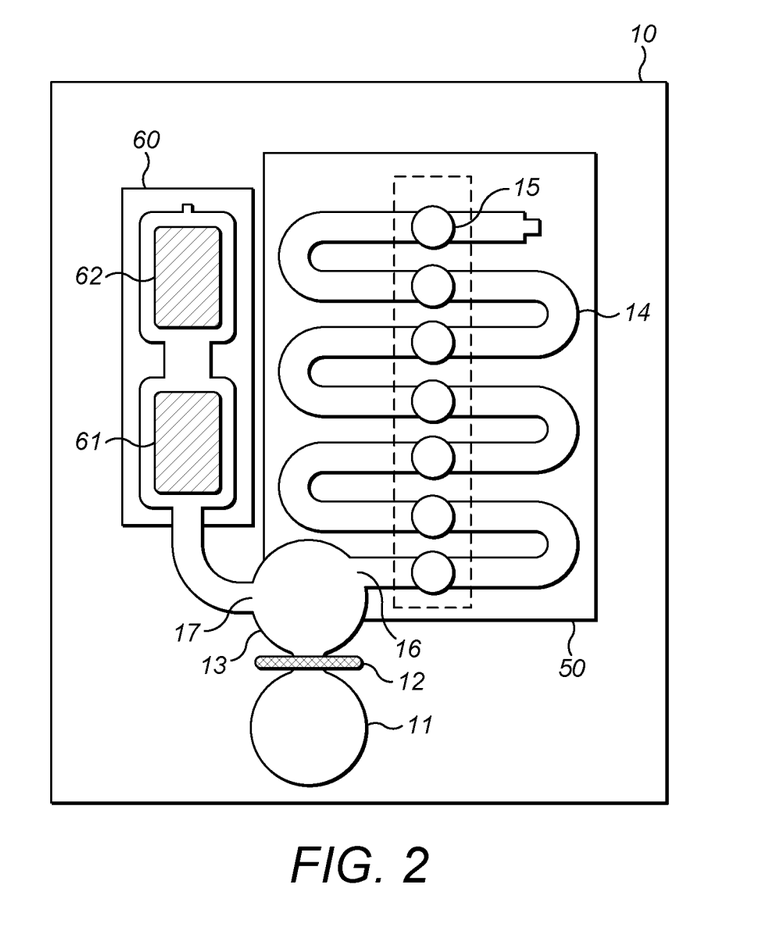
FIG. 2 shows a schematic view of a suitable arrangement of a physical detection unit and a biomarker detection unit in an assay device according to the first aspect of the invention.

FIG. 2 shows a schematic view of a suitable detection cartridge 10 comprising a physical detection unit 50 and a biomarker detection unit 60 for use in an assay device 1 according to the first aspect of the invention.

The physical detection unit 50 and the biomarker detection unit 60 are arranged to receive the same biological fluid sample from a patient, which in this example embodiment is whole blood. The whole blood is input into a sample application area 11 and passes through a plasma filter 12 into a receiving vessel 13.

From the receiving vessel 13, a portion of the blood plasma passes to the physical detection unit 50. The physical detection unit 50 is arranged to measure a viscosity of the blood plasma sample. The physical detection unit 50 comprises a capillary channel 14, which is curved so as to fit into a small space. However, it should be appreciated that any arrangement of the capillary channel 14 may be suitable. The physical detection unit 50 also comprises a plurality of optical detectors 15 spaced along the capillary channel 14. The optical detectors 15 detect movement of the blood plasma sample as it passes along the capillary channel 14. The device comprises a timer (not shown) which measures a series of time points as the blood plasma sample is detected by each of the optical detectors 15 passing through the capillary channel 14, so as to measure the time taken for the blood plasma sample to move along the capillary channel 14.

From the receiving vessel 13, another portion of the blood plasma passes to the biomarker detection unit 60. The biomarker detection unit 60 is arranged to detect and/or measure a biomarker in the biological fluid sample. In this example embodiment the biomarker detection unit 60 is arranged to detect and measure Procalcitonin levels in the biological fluid sample. However, additional and/or alternative biomarkers may be detected and measured in the biological fluid sample.

The biomarker detection unit 60 comprises a first cartridge 61 and a second cartridge 62. The first cartridge 61 acts as a baseline. In the second cartridge 62 Procalcitonin is detected and measured in the sample. The amount of Procalcitonin is determined by measuring a change in optical absorbance at a specified wavelength between the first and second cartridges. The biomarker detection unit 60 may alternatively or additionally be used to conduct infectious disease testing on the biological fluid sample, for example to conduct the TORCH test. Whilst FIG. 2 shows a single cartridge in which the biomarker assay is conducted, it is possible for the assay device to include additional cartridges in which further biomarker assays are conducted, as required for a particular disease.

FIG. 2 shows that the receiving vessel 13 includes two separate outputs, a first output 16 which leads to the capillary channel 14 of the physical detection unit 50 and a second output 17 which leads to the biomarker detection unit 60. In the example embodiment shown in FIG. 2, the first output 16 is located above the second output 17 so that in use the blood plasma sample that reaches the first output 16 passes to the capillary channel 14 of the physical detection unit and when the blood plasma sample drops below the first output 16 it reaches the lower second output 17 and passes to the biomarker detection unit 60. The blood plasma sample passes from the second output 17 to the biomarker detection unit 60 by means of a capillary channel, i.e. under capillary action. As the skilled person would appreciate, alternative ways of portioning the blood plasma sample to the physical detection unit 50 and biomarker detection unit 60 could be used.

Figure 3:
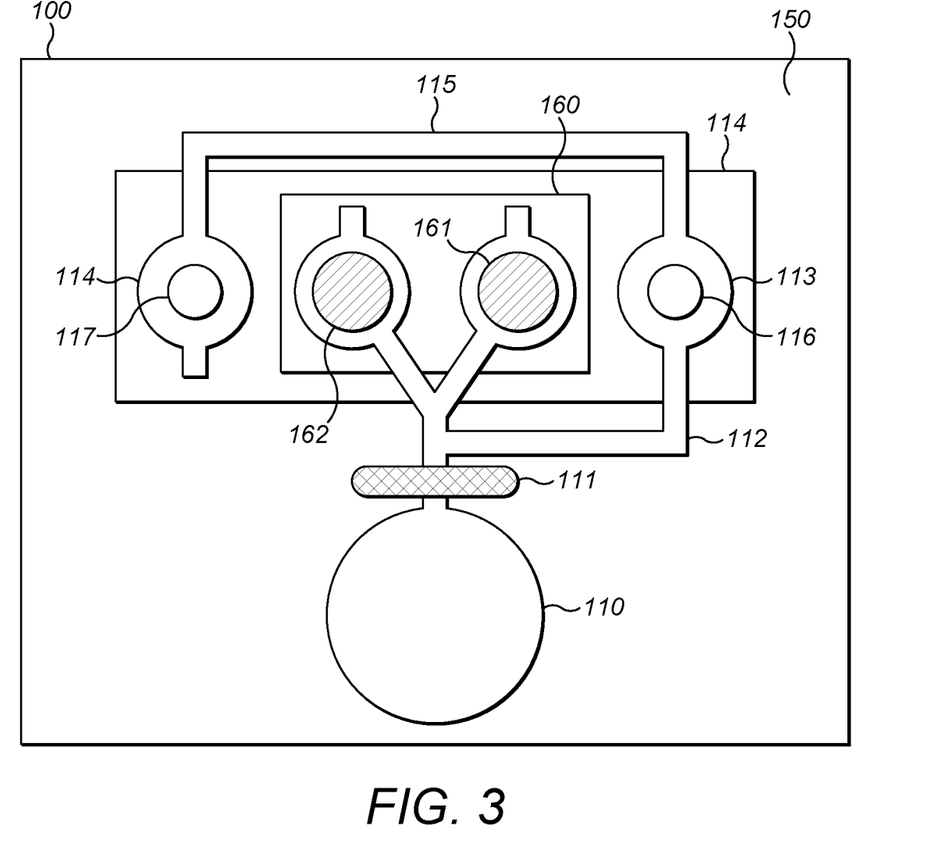
FIG. 3 shows a schematic view of an alternative suitable arrangement of a physical detection unit and a biomarker detection unit in an assay device according to the first aspect of the invention.

FIG. 3 shows a schematic view of an alternative suitable detection cartridge 100 comprising a physical detection unit 150 and a biomarker detection unit 160 for use in an assay device 1 according to the first aspect of the invention.

The physical detection unit 150 and the biomarker detection unit 160 are arranged to receive the same biological fluid sample from a patient, which in this example embodiment is whole blood. The whole blood is input into a sample cartridge 110 and passes through a plasma filter 111 into a channel 112.

From the channel 112, a portion of the blood plasma passes to the physical detection unit 150. The physical detection unit 150 is arranged to measure a viscosity of the blood plasma sample. The physical detection unit 150 comprises a baseline vessel 113, an endpoint vessel 114 and a capillary channel 115 extending from the baseline vessel 113 to the endpoint vessel 114. The capillary channel 115 is shaped so as to fit into a small space. However, it should be appreciated that any arrangement of the capillary channel 115 may be suitable. The physical detection unit 150 also comprises an optical detector 116 located at the baseline vessel 113 and an optical detector 117 located at the endpoint vessel 114. The optical detectors 116, 117 detect movement of the blood plasma sample as it passes from the baseline vessel 113 along the capillary channel 115 to the endpoint vessel 114. The device comprises a timer (not shown) which starts when the blood plasma sample is detected passing through the baseline vessel 113 and stops when the blood plasma sample is detected passing through the endpoint vessel 114, so as to measure the time taken for the blood plasma sample to move between these two points.

From the sample cartridge 110, another portion of the blood plasma passes to the biomarker detection unit 160.

The blood plasma sample passes from the sample cartridge 110 to the biomarker detection unit 160 by means of a capillary channel, i.e. under capillary action. The biomarker detection unit 160 is arranged to detect and/or measure a biomarker in the biological fluid sample. In this example embodiment the biomarker detection unit 160 is arranged to detect and measure Procalcitonin levels in the biological fluid sample. However, additional and/or alternative biomarkers may be detected and measured in the biological fluid sample.

The biomarker detection unit 160 comprises a first area 161 and a second area 162 in which Procalcitonin is detected and measured in the sample. The amount of Procalcitonin is determined by measuring a change in optical absorbance at a specified wavelength between the first and second areas. The biomarker detection unit 160 may alternatively or additionally be used to conduct infectious disease testing on the biological fluid sample, for example to conduct the TORCH test.

Figure 4:
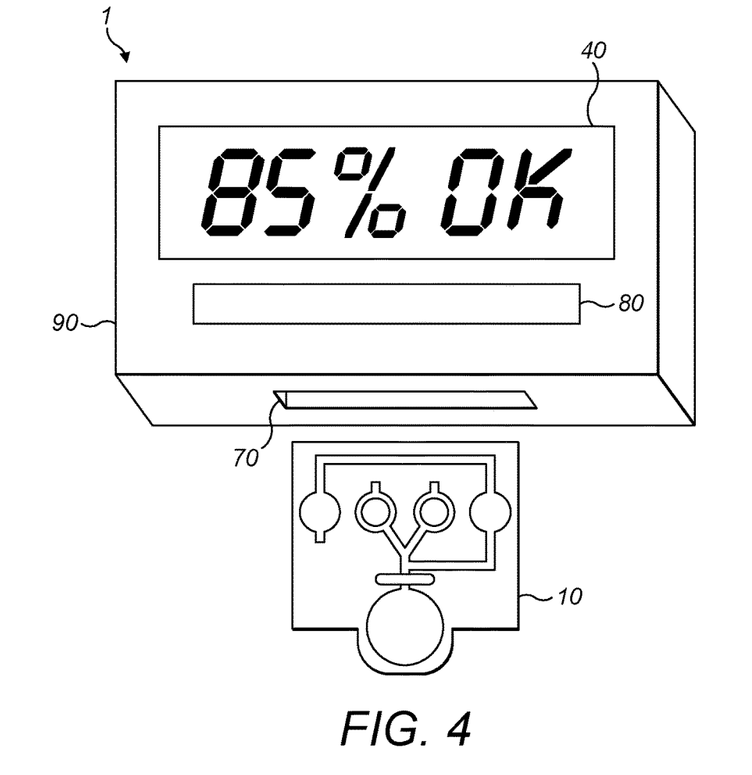
FIG. 4 shows a schematic view of a suitable arrangement of an assay device according to the first aspect of the invention including the physical detection unit of FIG. 3.

FIG. 4 shows a schematic view of a suitable arrangement of an assay device 1 according to the first aspect of the invention which comprises a housing 90 in which a cartridge slot 70 is located. The disposable detection cartridge 10 can be input into the assay device via the cartridge slot 70. The detection cartridge 10 can be removed from the assay device 1 after use. FIG. 4 shows a detection cartridge 10 as shown in FIG. 3 but any suitable detection cartridge according to the invention may be used. The assay device 1 shown in FIG. 4 comprises an output unit 40 in the form of a display and a user input unit 80. The user input unit 80 is used to input information, for example about the patient. The memory unit 20 and the processing unit 30 are not shown in FIG. 4 but are housed internally beneath the output unit 40 and user input unit 80.

Figure 5:
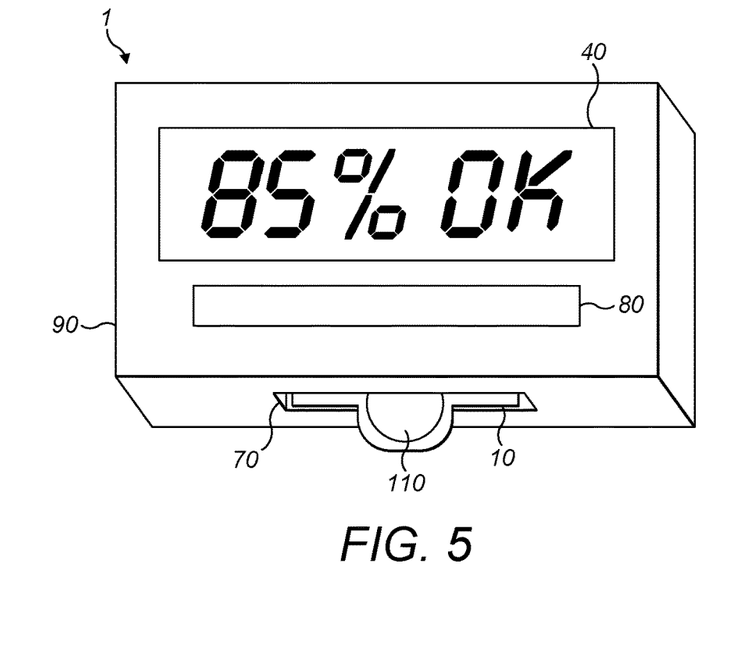
FIG. 5 shows a schematic view of the assay device shown in FIG. 4 after the cartridge has been inserted.

FIG. 5 shows the assay device 1 of FIG. 4 in which the detection cartridge 10 has been inserted, i.e. by means of the cartridge slot 70. The sample cartridge 110 extends from the housing of the assay device 1 to enable easy input of the biological fluid sample. Other arrangements for the input of the biological fluid sample may be used however.

Figure 6:
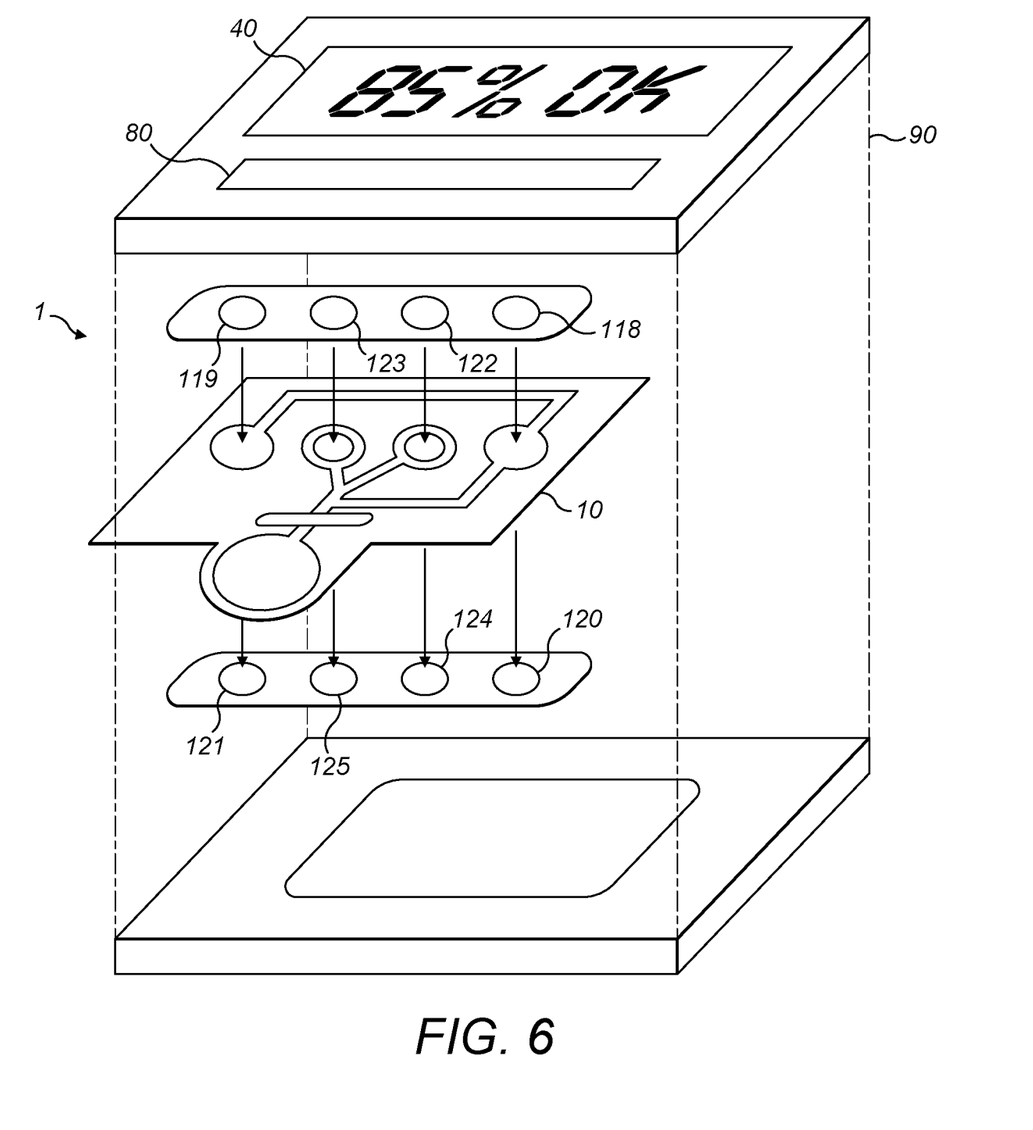
FIG. 6 shows an internal schematic view of the assay device shown in FIG. 4.

FIG. 6 shows an internal schematic view of the assay device shown in FIG. 4. In the arrangement shown in FIG. 6, when input into the assay device 1, the detection cartridge 10 is located substantially internally within the housing 90 and beneath the output unit 40 and the user input unit 80. The memory unit 20 and the processing unit 30 are not shown in FIG. 6 but are housed internally beneath the output unit 40 and user input unit 80. The optical detectors 116, 117 each comprise an optical emitter 118, 119 and an optical detector 120, 121. In this example embodiment the biomarker detection unit 160 is arranged to detect and measure Procalcitonin levels in the biological fluid sample by means of colorimetric measurements. The colorimetric measurements are made by means of optical emitters 122, 123 and optical detectors 124, 125.

Figure 7:
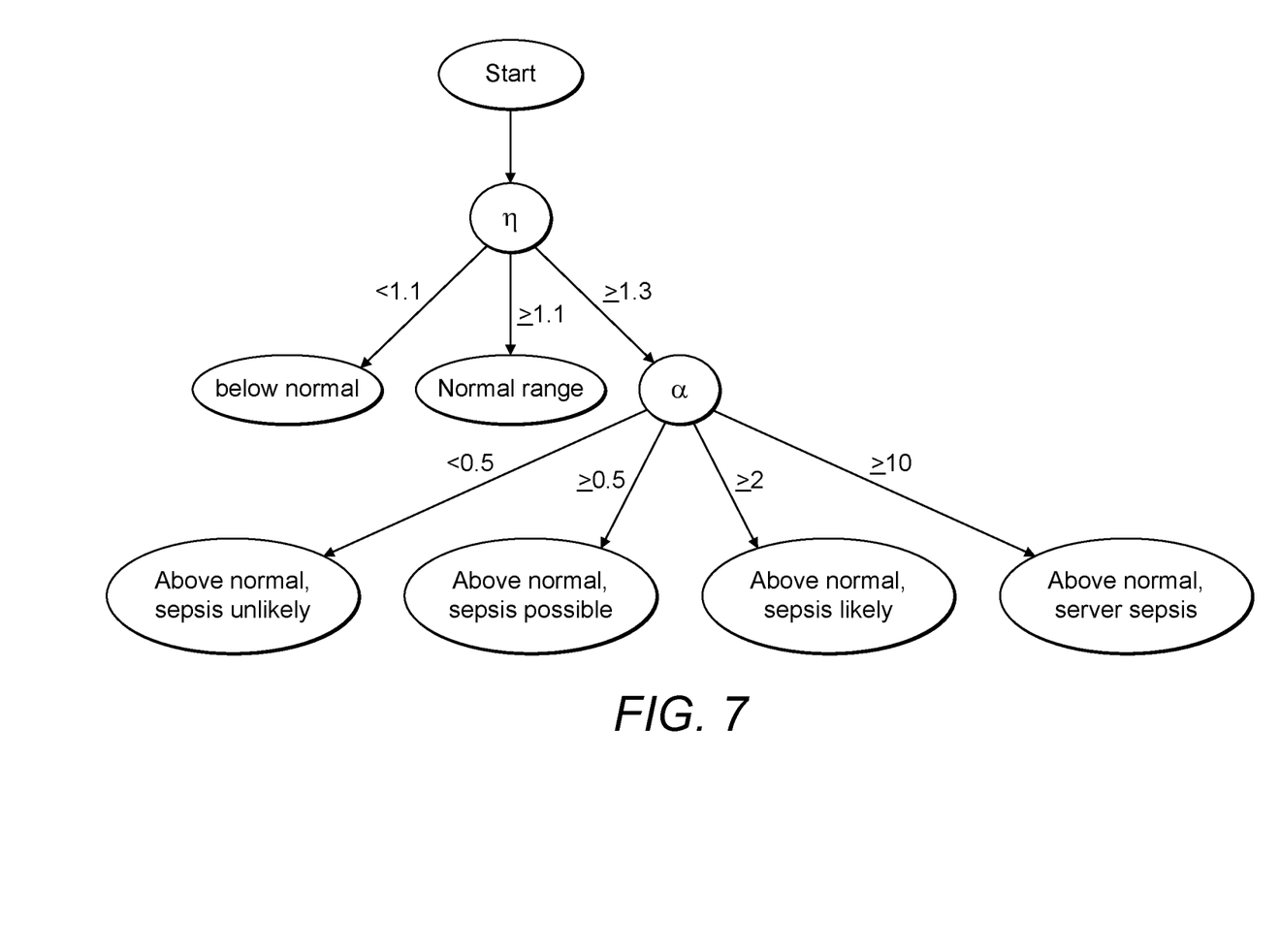
FIG. 7 shows an example flow diagram illustrating steps of a method of generating an output which is a diagnosis of a disease according to the second aspect of the invention.

FIG. 7 shows an example flow diagram illustrating steps of a method of generating an output which is a diagnosis of sepsis.

In the first step, the measured dynamic viscosity value is compared to the values for a healthy adult and determined either as below the normal value, normal or above the normal value. If the measured dynamic viscosity value is above the normal value then, in the next step, the measured Procalcitonin level is the compared to the values for a healthy adult.

As shown in FIG. 7, when the measured value of Procalcitonin concentration is higher than about 0.5 ng/ml, then the output is that the patient may have an infectious disease but sepsis is unlikely. When the measured value of Procalcitonin concentration is higher than about 0.5 ng/ml and lower than about 2 ng/ml then the output is that the patient may have a systemic infection and sepsis is possible. When the measured value of Procalcitonin concentration is higher than about 2 ng/ml and lower than about 10 ng/ml then the output is that the patient is likely to have a systemic infection and sepsis is likely. When the measured value of Procalcitonin concentration is higher than about 10 ng/ml then the output is that the patient has a major systemic inflammatory response indicative of sepsis.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, and drawings), or to any novel one, or any novel combination, of the steps of any method or process so disclosed.

The invention claimed is:

1. An assay device for use with samples of biological fluid, the assay device comprising:
 a physical detection unit for measuring a viscosity of a biological fluid sample, wherein the physical detection unit includes a capillary channel and measures a rate of movement of the biological fluid sample as the biological fluid sample passes along the capillary channel;
 a biomarker detection unit for detecting and/or measuring a biomarker in the biological fluid sample; and
 a receiving vessel in fluidic communication with the physical detection unit and the biomarker detection unit, the receiving vessel configured to direct a first portion of the biological fluid sample to the capillary channel of the physical detection unit, and a second portion of the biological fluid sample to the biomarker detection unit,
 wherein the receiving vessel is sized to receive a volume of the biological fluid sample sufficient to flow into the physical detection unit and the biomarker detection unit, and
 the biological fluid sample flows through the assay device under capillary action without a need for an external pump, and
 wherein the physical detection unit further comprises:
 a baseline vessel;
 an endpoint vessel;
 a first optical detector positioned at the baseline vessel;

a second optical detector positioned at the endpoint vessel, and wherein the capillary channel of the physical detection unit extends from the baseline vessel to the endpoint vessel, and wherein the first optical detector and the second optical detector detect movement of the biological fluid sample as the biological fluid sample moves from the baseline vessel along the capillary channel to the endpoint vessel.

2. An assay device according to claim 1, wherein the biomarker detection unit is configured to detect and/or measure at least one biomarker in the biological fluid sample, wherein the at least one biomarker is selected from one or more of Procalcitonin, C-reactive protein (CRP), cytokines, alpha-fetoprotein, beta-2-microglobulin, calcitonin, immunoglobulins, D-dimer and troponin.

3. An assay device according to claim 1, wherein the biomarker detection unit comprises at least one vessel in which a biological assay is conducted.

4. An assay device according to claim 1, wherein the physical detection unit and the biomarker detection unit are housed in a removable and/or disposable detection cartridge.

5. An assay device according to claim 4, wherein the detection cartridge comprises a lab on a chip unit.

6. An assay device according to claim 1, further comprising a removable and/or disposable sample cartridge.

7. An assay device according to claim 1, further comprising a molecular amplification unit located at or near to a fluid introducing portion.

8. An assay device according to claim 1, further comprising:

a processing unit arranged to operate on the viscosity and biomarker measurements to determine an output; and an output unit arranged to provide the output to a user, wherein the first optical detector and the second optical detector of the physical detection unit measure the rate of movement of the biological fluid sample as the first portion of the biological fluid sample passes along the capillary channel, and wherein the biomarker detection unit detects and/or measures the biomarker in the biological fluid sample as the second portion of the biological fluid sample passes along the biomarker detection unit.

9. An assay device according to claim 8, further comprising a memory unit to store the viscosity and biomarker measurements.

10. An assay device according to claim 8, wherein the processing unit is arranged to operate to determine an output which is a diagnosis of a disease and/or which is indicative of a disease state for a patient, wherein the disease is selected from one or more of an infectious disease, arthritis, cancer and stroke.

11. An assay device according to claim 10, wherein the disease is sepsis.

12. A method of generating an output, the method comprising: receiving a biological fluid sample from a patient at an assay device, wherein the assay device comprises a physical detection unit having a capillary channel, a biomarker detection unit, and a receiving vessel in fluidic communication with the physical detection unit and the biomarker detection unit, the receiving vessel sized to receive a volume of the biological fluid sample sufficient to flow into the physical detection unit and the biomarker detection unit; directing a first portion of the biological fluid sample to the capillary channel of the physical detection unit; directing a second portion of the biological fluid sample to the biomarker detection unit; obtaining a viscosity measurement of the first portion of the biological fluid sample that passes along the capillary channel of the physical detection unit; obtaining a biomarker measurement by detecting and/or measuring a biomarker in the second portion of the biological fluid sample that passes along the biomarker detection unit; and operating on the viscosity and biomarker measurements to determine the output, wherein the physical detection unit further comprises: a baseline vessel; an endpoint vessel; a first optical detector positioned at the baseline vessel; a second optical detector positioned at the endpoint vessel, and wherein the capillary channel of the physical detection unit extends from the baseline vessel to the endpoint vessel, wherein the obtaining the viscosity measurement further comprises measuring a rate of movement of the biological fluid sample by the first optical detector and the second optical detector detecting movement of the biological fluid sample as the first portion of the biological fluid sample moves from the baseline vessel along the capillary channel to the endpoint vessel, and wherein the biological fluid sample flows through the assay device under capillary action without a need for an external pump.

13. A method according to claim 12, further comprising storing the viscosity and biomarker measurements in a memory unit.

14. A method according to claim 12, wherein: the biomarker is selected from an amount and/or presence of at least one biomarker in the biological fluid sample, wherein the at least one biomarker is selected from one or more of Procalcitonin, C-reactive protein (CRP), cytokines, alpha-fetoprotein, beta-2-microglobulin, calcitonin, immunoglobulins, D-dimer and troponin; and wherein the biomarker is indicative of a disease selected from one or more of an infectious disease, arthritis, cancer and stroke.

15. A method according to claim 14, wherein the disease is sepsis.

16. An assay device according to claim 1, wherein the assay device further comprises a filter in fluidic communication with both the physical detection unit and the biomarker detection unit.

17. An assay device according to claim 8, wherein the processing unit is configured to operate on measurements of a series of time points that the biological fluid sample is detected by the at least one detectors as the first portion of the biological fluid sample passes along the capillary channel.

18. An assay device for use with a biological fluid sample, the assay device comprising:

a physical detection unit configured to obtain a viscosity measurement of the biological fluid sample, the physical detection unit comprising:

a baseline vessel;

an endpoint vessel;

a first optical detector positioned at the baseline vessel;

a second optical detector positioned at the endpoint vessel, and a capillary channel of the physical detection unit extends from the baseline vessel to the endpoint vessel, and wherein the first optical detector and the second optical detector detect movement of the biological fluid sample as a first portion of the biological fluid sample moves from the baseline vessel along the capillary channel to the endpoint vessel;

a biomarker detection unit configured to obtain a biomarker measurement in the biological fluid sample as a second portion of the biological fluid sample passes the biomarker detection unit;

a processing unit arranged to operate on the obtained viscosity and biomarker measurements to determine an output; and an output unit arranged to provide the output to a user.

19. An assay device according to claim 18, wherein the assay device further comprises a receiving vessel in fluidic communication with the physical detection unit and the biomarker detection unit and directs the first portion of the biological fluid sample to the physical detection unit, and the second portion of the biological fluid sample to the biomarker detection unit, wherein the receiving vessel is sized to receive a volume of the biological fluid sample sufficient to flow into each of the physical detection unit and the biomarker detection unit.

* * * * *